United States Patent [19]
von Philipp

[11] 4,077,183
[45] Mar. 7, 1978

[54] MACHINE FOR THE AUTOMATIC ASSEMBLY OF VAPORIZERS

[75] Inventor: Fritz von Philipp, Neuburg, Germany

[73] Assignee: Firma Globol-Werk GmbH, Neuburg, Germany

[21] Appl. No.: 781,061

[22] Filed: Mar. 24, 1977

[51] Int. Cl.² .................. B65B 29/00; B65B 63/04
[52] U.S. Cl. .......................... 53/111 R; 53/111 RC; 53/120; 53/239; 53/252; 53/281
[58] Field of Search ............ 53/111 R, 111 RC, 116, 53/117, 120, 239, 250, 252, 281, 282

[56] References Cited

U.S. PATENT DOCUMENTS

| | | | |
|---|---|---|---|
| 3,645,063 | 2/1972 | Foirest | 53/111 RC |
| 3,919,827 | 11/1975 | Larson et al. | 53/120 X |

*Primary Examiner*—Robert Louis Spruill
*Attorney, Agent, or Firm*—Karl F. Ross

[57] ABSTRACT

Vaporizers with flat wicks folded into U-shape within open-topped, laterally apertured generally prismatic casings, capped by complementary covers which are vertically slidable thereon to control the escape of a volatile liquid impregnating the wicks, are mass-produced on a plurality of assembly lines each comprising a wick-loading station, an impregnating station, an insertion station and a capping station. The dry and unfolded wicks are successively advanced from their loading station along an upper track past the impregnating station, where they are permeated with the liquid, to the insertion station in which a plunger thrusts each wick through a narrow central slit into an aligned casing waiting on a lower track, the wick being doubled in passing through the slit into the casing. The filled casings travel on the lower track to the capping station where they are fitted with covers as they pass under a flat end of an arcuate tube through which the covers are delivered from a supply chute by an oscillating arm. The several assembly lines terminate at a common turntable from which their vaporizers are discharged to a packaging station.

10 Claims, 12 Drawing Figures

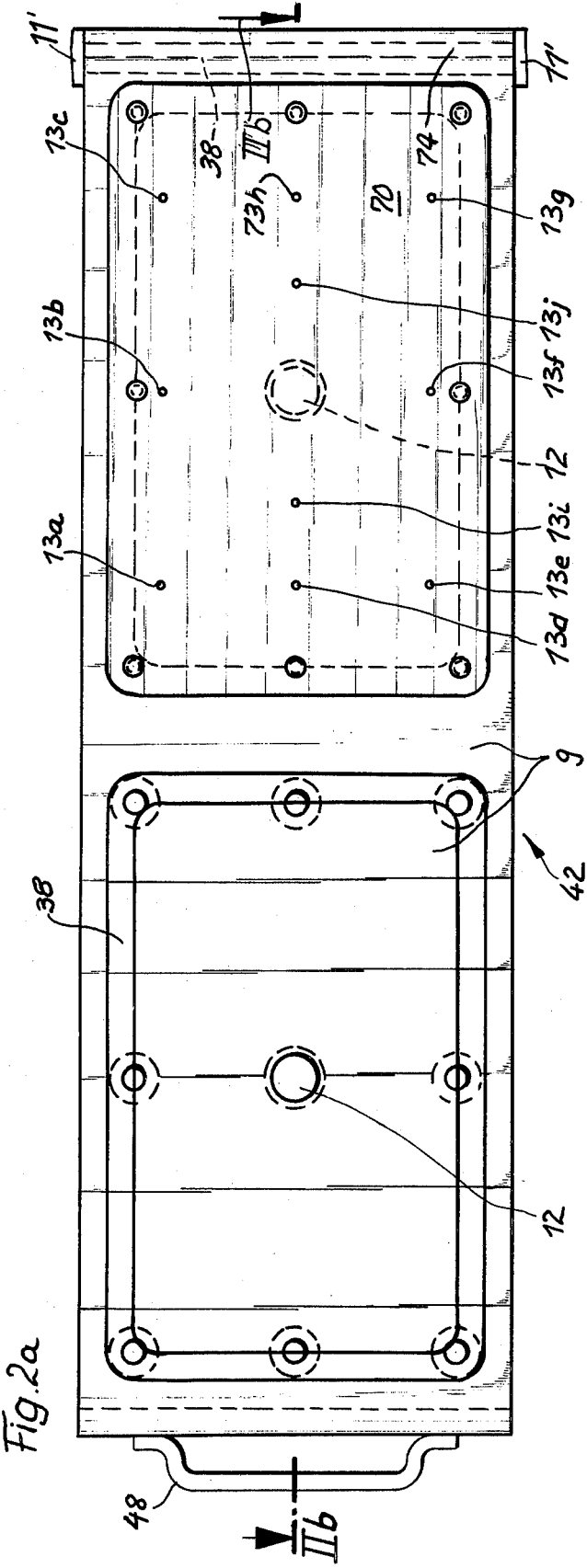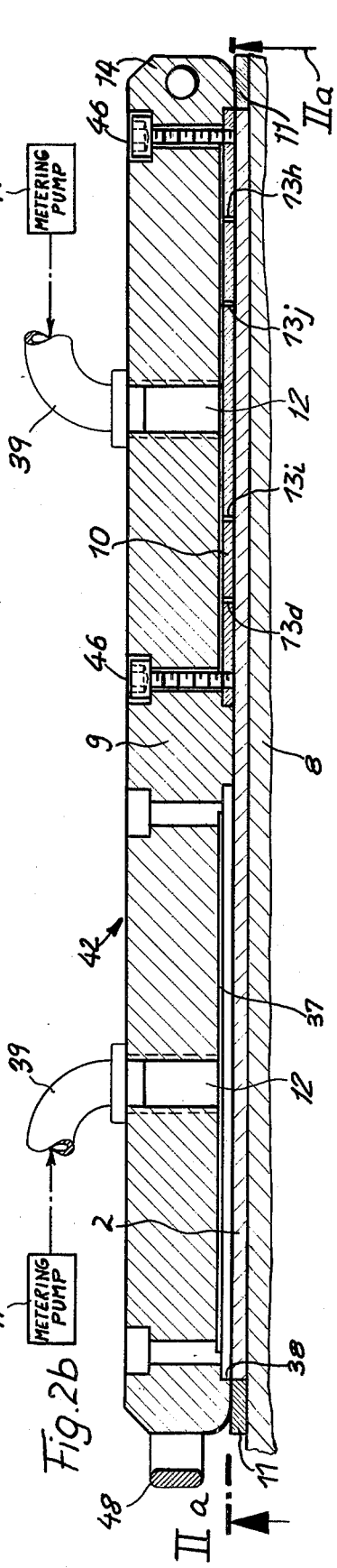

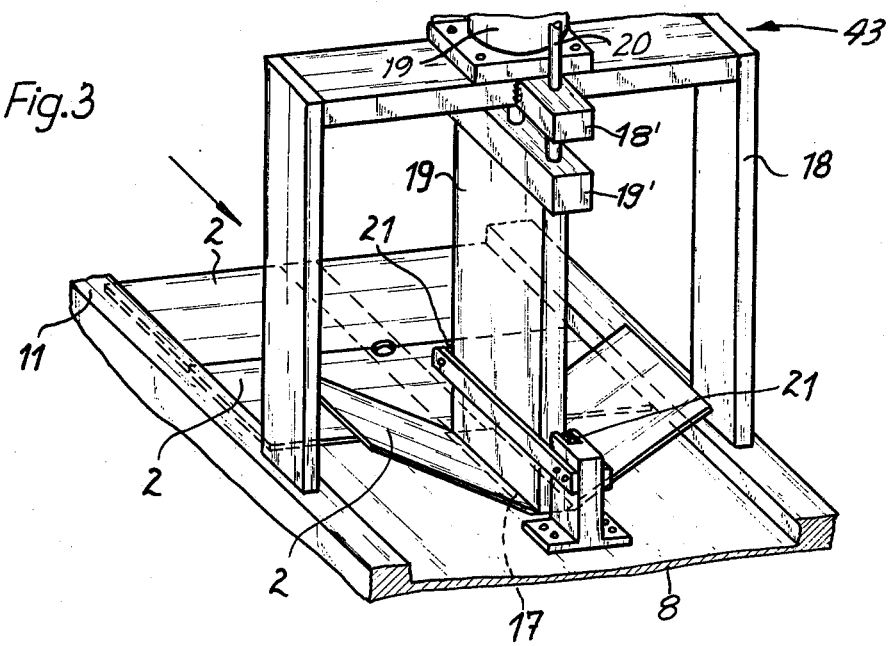
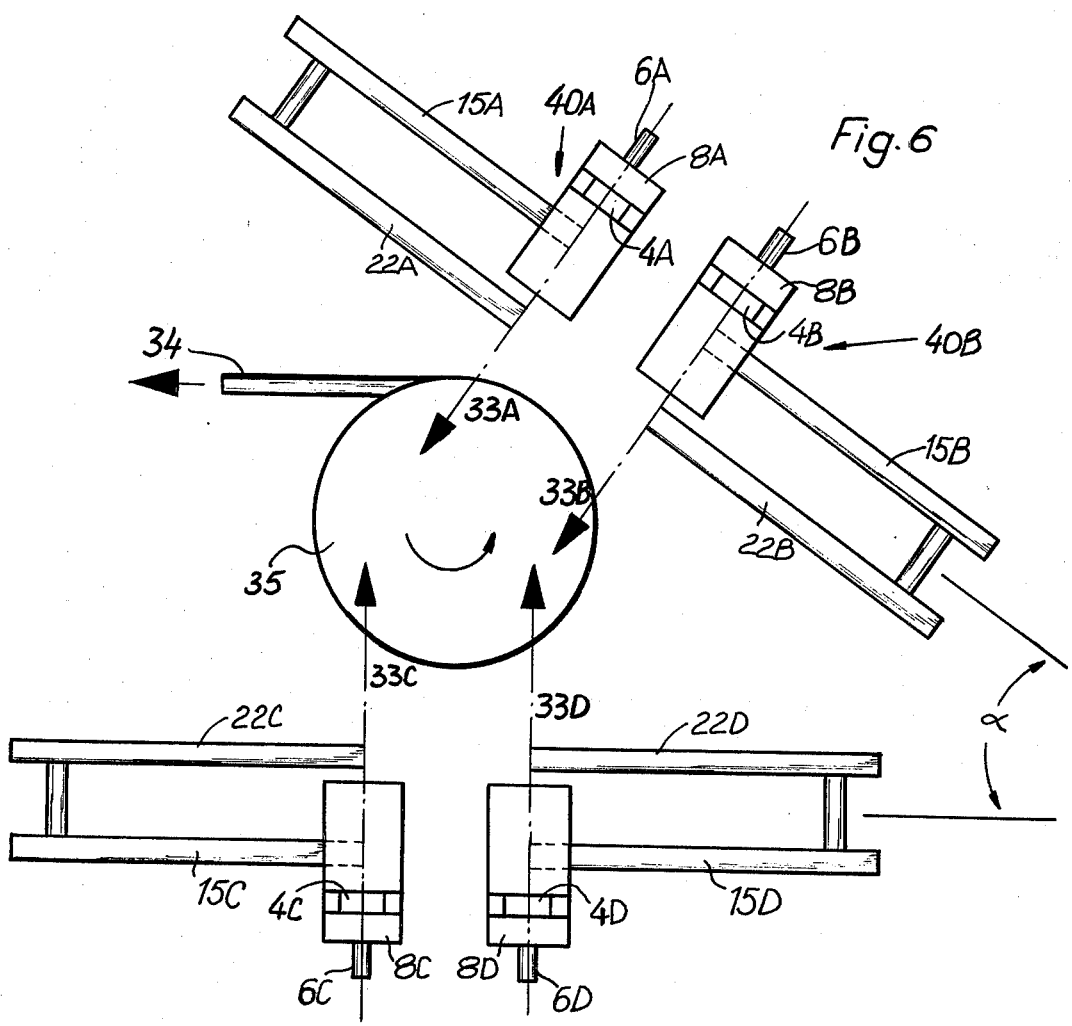

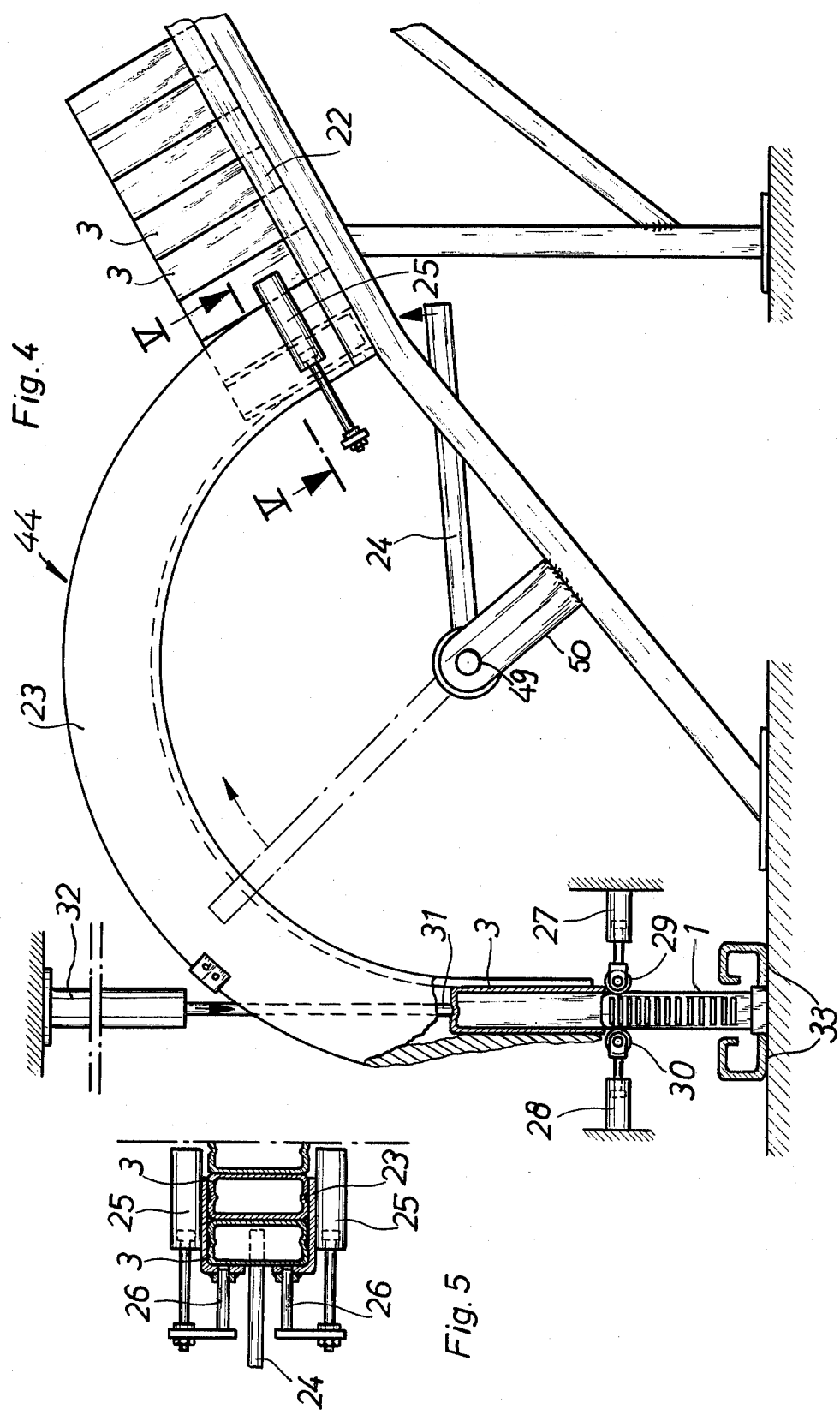

MACHINE FOR THE AUTOMATIC ASSEMBLY OF VAPORIZERS

FIELD OF THE INVENTION

My present invention relates to a machine designed for the automatic assembly of vaporizers of the type wherein a porous carrier or wick, permeated by a volatile liquid, is received in a casing with apertured sides which during periods of nonuse are overlain by a cover, the latter being slidable along the casing to expose larger or smaller portions of its apertured surface in order to control the escape of vapors from the wick. Vaporizers of this description can be used for the release of odoriferous substances having the character of insecticides, air fresheners or perfumes, for example.

BACKGROUND OF THE INVENTION

It has already been proposed to design the casing of such a vaporizer as a prismatic open-topped container of rectangular cross-section, the wick being a flat strip folded upon itself and received in the casing with its bight parallel to the major sides of the rectangle; the cover is of corresponding prismatic shape and has a height substantially equal to that of the casing. Reference may be made in this connection to U.S. design-patent application Ser. No. 763,661 filed Jan. 28, 1977 by Georg Schimanski.

OBJECTS OF THE INVENTION

The general object of my present invention is to provide a machine for automatically assembling the constituents of such vaporizers, namely their casings, wicks and covers, into complete units ready for shipment.

A more particular object is to provide means in such a machine for impregnating their wicks, as uniformly as possible, with the volatile liquid which is to be dispensed.

SUMMARY OF THE INVENTION

In accordance with my present invention, a machine of the character set forth comprises one or more assembly lines each including a frame which forms an upper track and a lower track. Dry, unfolded wicks are successively deposited on the upper track, at a loading station, by first feed means advancing the wicks in a row toward a transfer point where this track has a discontinuity, such as a narrow slit, giving access to the lower track. The advance of the wicks preferably occurs in steps, the first feed means comprising for this purpose an intermittently operating element such as a reciprocating slider. Each wick, on its way to the transfer point, passes an impregnating station provided with distributing means connected to a source of volatile liquid as discussed above. After having been permeated by a preferably pedetermined quantity of that liquid, the wicks continue to an insertion station at the aforementioned transfer point where each wick arrives concurrently with an associated casing moved along the lower track by second feed means synchronized with the first feed means. The second feed means may include a reciprocating piston driving each oncoming casing along that lower track in line with other casings previously deposited thereon, thereby intermittently moving an entire row of casings past the transfer point between an upstream location and a downstream location. When a wick and an associated casing are aligned with each other and register with the discontinuity of the upper track, a plunger at the insertion station forces the wick through that discontinuity into the casing, the plunger being aligned with a transverse centerline of the wick whereby the latter is doubled upon entering the casing. As each casing filled with an impregnated wick reaches a capping station at the aforementioned downstream location, an associated cover is positioned above the casing by third feed means synchronized with the first and second feed means as well as with the plunger of the insertion station; a pusher at the capping station then thrusts the cover onto the aligned casing to complete the assembly.

Advantageously, pursuant to another feature of my invention, the covers are individually guided to their position of alignment with the associated casings through a curved tube centered on the fulcrum of a swingable arm which forms part of the third feed means. The arm may coact with a conveyor such as a chute delivering a stack of covers to the entrance end of the guide tube whose flattened exit end overlies the path of the casings.

BRIEF DESCRIPTION OF THE DRAWING

The above and other features of my invention will now be described in detail with reference to the accompanying drawing in which:

FIG. 2a is a bottom view of a liquid-distributing unit, forming part of an impregnating station shown in FIG. 1, as seen on the line IIa — IIa of FIG. 2b;

FIG. 2b is a cross-sectional view taken on the line IIb — IIb of FIG. 2a;

FIG. 3 is a perspective view of an insertion station also shown in FIG. 1;

FIG. 4 is a somewhat diagrammatic elevational view, with parts broken away, of a capping station likewise shown in FIG. 1;

FIG. 5 is a sectional detail view taken on the line V — V of FIG. 4;

FIG. 6 is a schematic plan view of the overall layout of a machine comprising several assembly lines as shown in FIG. 1;

SPECIFIC DESCRIPTION

Figure 7:
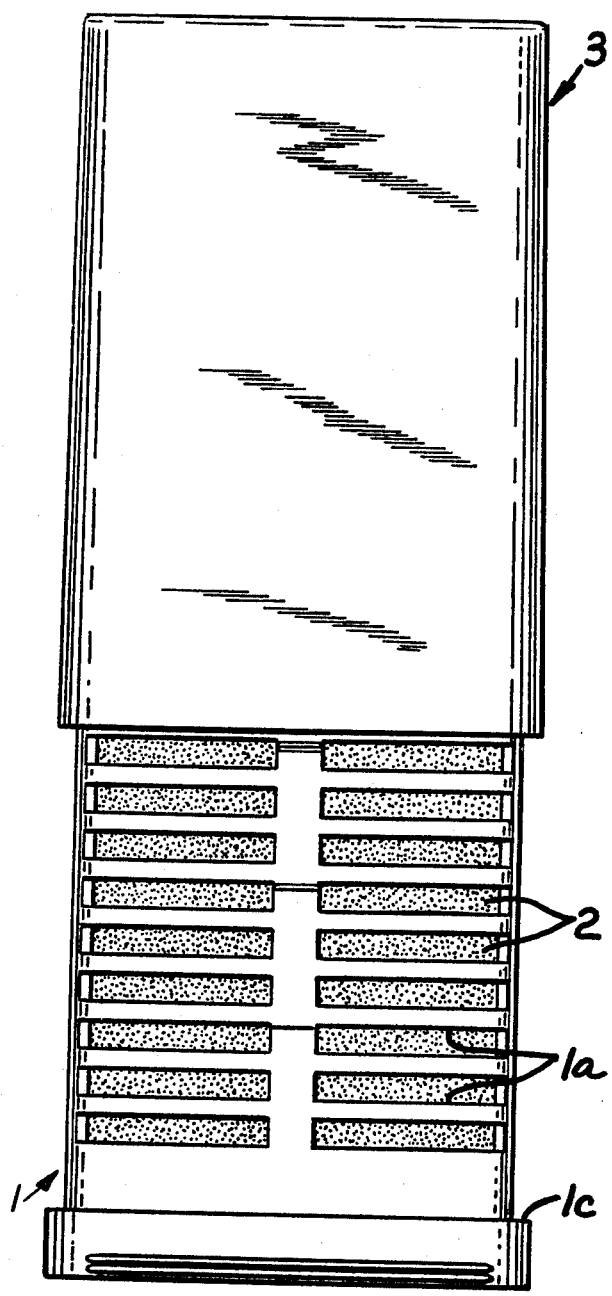
FIG. 7 is a side-elevational view of a partly opened vaporizer assembled on the machine of FIGS. 1 – 6.
Figure 8:
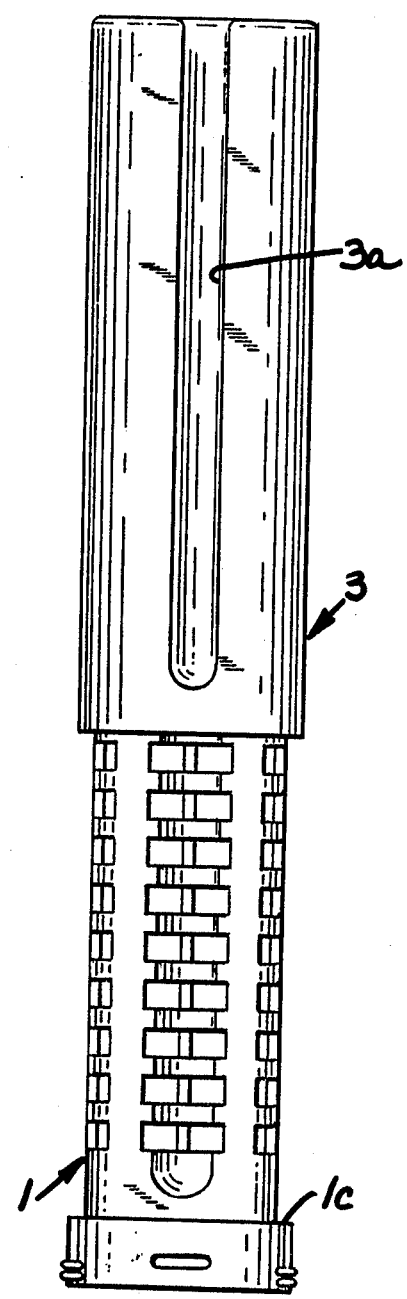
FIG. 8 is an end-elevational view of the vaporizer shown in FIG. 7.
Figure 9:
FIG. 9 is a top view of the same vaporizer.
Figure 10:
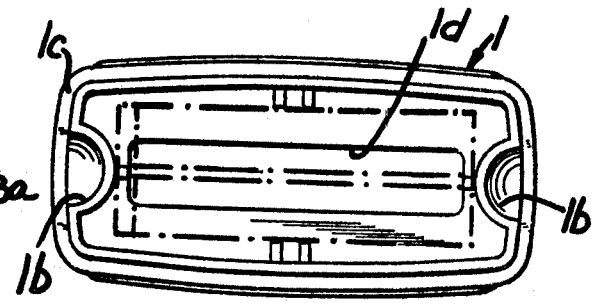
FIG. 10 is a top view of the vaporizer casing with its cover and wick removed.
Figure 11:
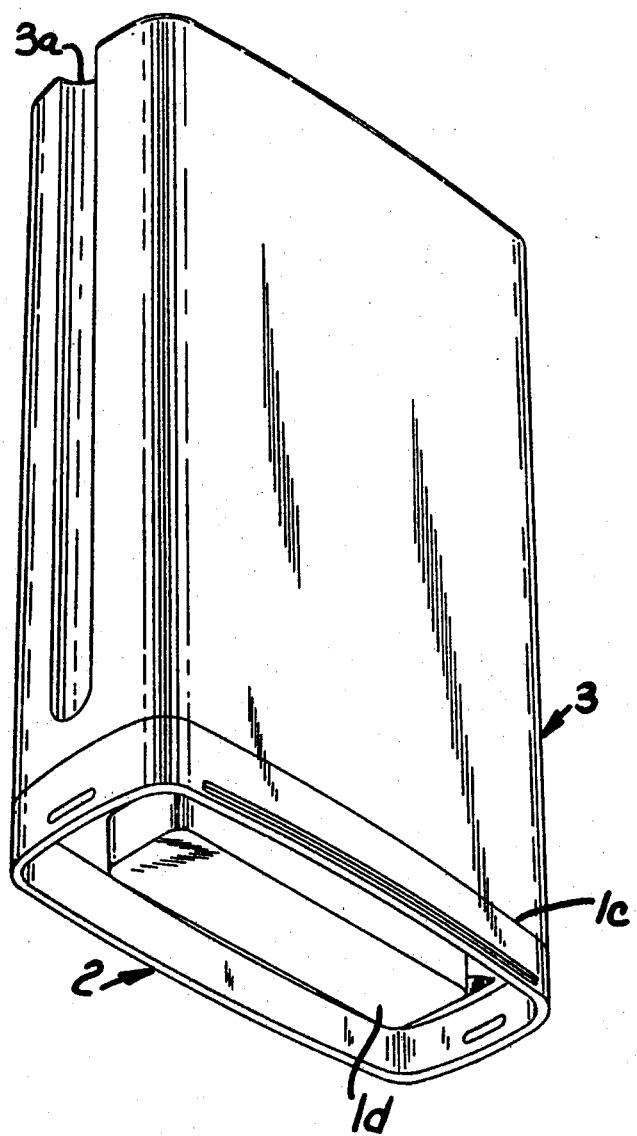
FIG. 11 is a perspective side and bottom view of the closed vaporizer.

Reference will first be made to FIGS. 7 – 11 illustrating a vaporizer of the type to which my invention is applicable. The vaporizer comprises an open-topped casing 1 of generally prismatic shape and substantially rectangular horizontal cross-section, made preferably of plastic material such as polypropylene or polyethylene, and a complementary cover 3 of similar material. The side and end walls of casing 1 have apertures 1a through which is visible a cellulosic wick 2 permeated by a volatile air freshener or other odoriferous liquid. As indicated in dot-dash lines in FIG. 10, wick 2 is a flat strip folded in half within casing 1 so as to form a U-shaped insert with upstanding arms. Apertures 1a can be selectively uncovered by an upward sliding of cover 3 as seen in FIGS. 7 and 8. Casing 1 has lateral indentations 1b, accommodating internal ribs 3a of cover 3, as well as a shoulder 1c forming a bottom stop for the cover. A well 1d serves as a receptacle for excess liquid.

Figure 1:
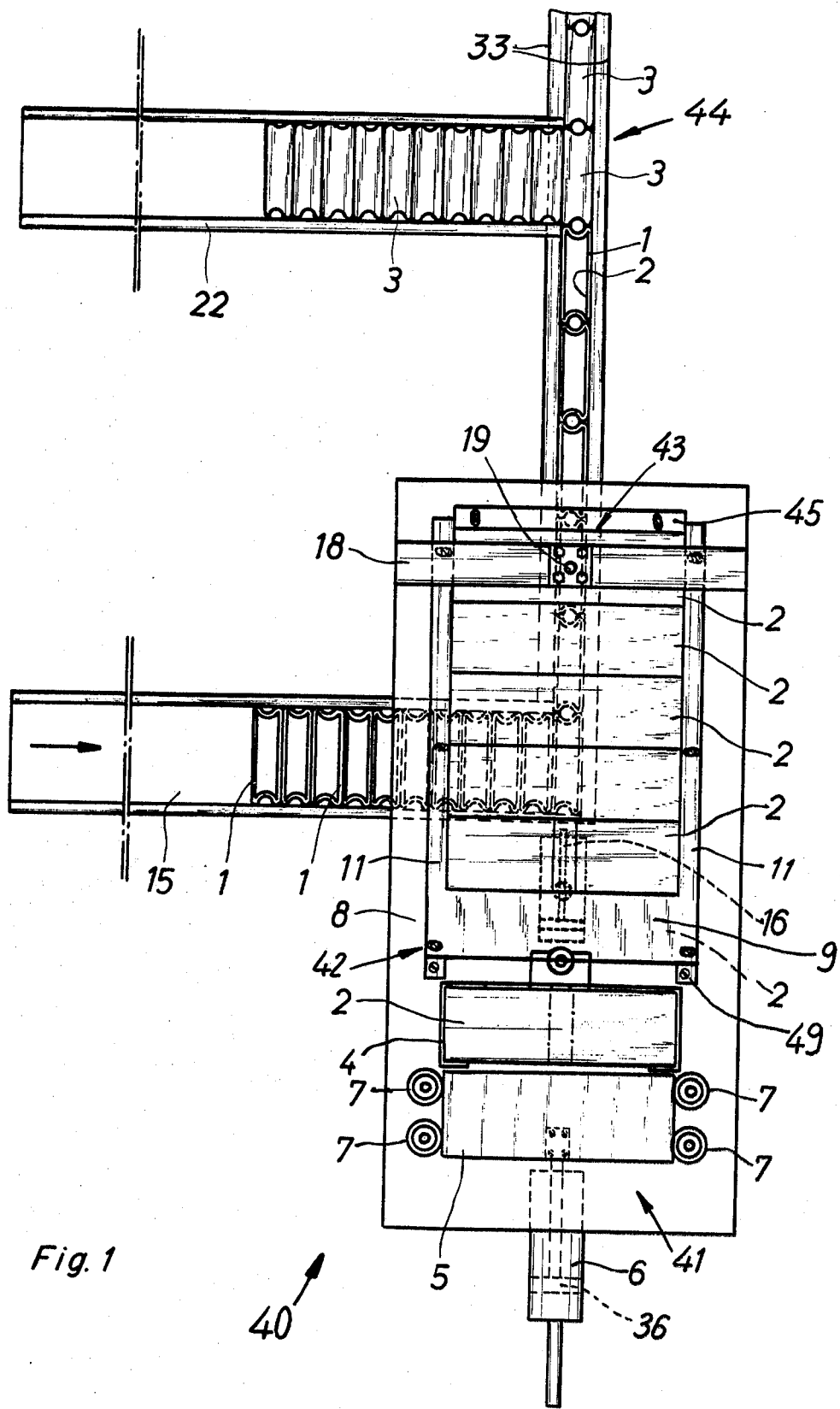
FIG. 1 is a somewhat diagrammatic top view of an assembly line forming part of a machine according to my invention.

In FIG. 1 I have shown an assembly line 40 representative of several such lines designated 40A, 40B, 40C, 40D in FIG. 6. Assembly line 40 comprises a frame forming a platform 8 at an upper level and a pair of rails 33 at a lower level, platform 8 forming an upper track for the transportation of wicks 2 whereas rails 33 constitute a lower track for the guidance of casings 1. Assembly line 40 further comprises a loading station 41 at one end of platform 8, an impregnating station 42 farther along the track formed by this platform, an insertion station 43 at a transfer point between the two tracks, and a capping station 44 at an extension of the lower track downstream of the transfer point.

The upper track is laterally bounded by a pair of sills 11 whose separation substantially equals the length of a wick 2 in its unfolded state. The dry and unfolded wicks are successively deposited on platform 8, at station 41, by a vertical hopper 4 rising from that platform, the hopper containing a stack of such wicks and being provided at the level of the lowest wick (i.e. just above platform 8) with aligned front and rear slots through which a slider 5 may enter to push the lowest wick broadside out of the hopper and into impregnating station 42. Slider 5, whose height and length substantially equal the corresponding dimensions of a wick, is laterally guided by rollers 7 and is reciprocated by a servomotor 6, such as a pneumatic cylinder, with a stroke length exceeding the width of the wicks as measured in the transport direction, Sills 11 are adjustably secured to platform 8 by screws 49, as is an end stop 45 just beyond insertion station 43.

Impregnating station 42, as more clearly shown in FIGS. 2a and 3b, comprises an upper plate 9 spanning the sills 11 and forming two clearances 37 just above the level of these sills, the clearances being rabbeted at 38 to accommodate a pair of lower plates 10 of which only the right-hand plate has been illustrated in FIGS. 2a and 2b. Plates 9 and 10 are interconnected by screws 46 and form a continuous bottom surface just above the path of the wicks 2 whose height is slightly less than that of the sills 11. Impregnating liquid is delivered by two metering pumps 47 (or possibly by a single pump) via respective conduits 39 to a pair of perforations 12 in plate 9 opening onto the two clearances 37 whereby a small pool of liquid accumulates in the gap between plate 9 and each plate 10; each of the latter plates, acting as a distributor for the liquid, is provided with a multiplicity of perforations 13a – 13j, the first six perforations 13a – 13h forming a rectangular array while the two remaining perforations 13i and 13j lie on the longitudinal centerline of that array and of the underlying wick 2 so as to define with perforations 13b and 13f a diamond-shaped figure such as a square or a rhombus. I have found that with such an array of perforations, and with accurate dosing of the supplied liquid by the metering pump or pumps 47, the impregnation of the wicks will be highly uniform and will vary by only a few percentage points from one wick to the next.

As further shown in FIGS. 2a and 2b, impregnating unit 9, 10 is hinged at 14 to lugs 11' rising from the right-hand sill 11 and is provided at its left side with a handle 48 to facilitate the temporary removal of distributing plates 10 for cleaning purposes. Narrow gaskets of rubber or the like, not shown, may be interposed between plates 9 and 10 to prevent the leakage of fluid from clearances 37.

Metering pumps 47 may be piston pumps with an adjustable stroke.

A conveyor 15, which could be a chute or an intermittently driven transport belt, carries a series of casings 1 toward rails 33 which define a track of generally C-shaped profile, as best seen in FIG. 4; the left-hand rail is cut away at the junction of this track with conveyor 15 to let a single casing, in an upright position, enter the track with its major sides parallel to the rails. A plunger 16, reciprocating in synchronism with slider 5 and with the pistons of metering pumps 47, advances each oncoming casing along the channel of rail 33 so that the open top of the casing lies just below the platform 8. Thus, the casings 1 reach the lower track at a location upstream of insertion station 43, the stroke length of piston 16 being so chosen with reference to the width of the wicks 2 that a wick and a casing arrive simultaneously at that insertion station. In the present instance the distance between impregnating station 42 and insertion station 43 corresponds to the width of six wicks, it being assumed that six operating cycles of the machine are required for a thorough wetting of the wicks by the impregnating liquid.

As seen in FIG. 3, platform 8 is provided at station 43 with a narrow slit 17 extending longitudinally in the middle of the two tracks so as to register with the mouth of a casing on the lower track formed by rail 33 (not visible in FIG. 3) when the casing comes to rest in line with a wick 2 at the end of a cycle. At this instant a plunger 19, guided in a portal 18 above platform 8, is depressed (e.g. pneumatically) to penetrate the slit 17 whose width exceeds the thickness of the plunger by slightly more than twice the wick thickness. With the wicks prescored at opposite sides of their transverse centerlines, as indicated in dot-dash lines in FIGS. 1 and 3, the thrust of plunger 19 forces the middle part of the wick through the slit 17 into the underlying casing 1 while its impregnated wings rise alongside the plunger and fold along the score lines whereby the wick is doubled upon being introduced into the casing. With the casing mouth slightly wider than the slit 17, the two upstanding arms of the U-shaped wick separate somewhat after clearing the slit so as to abut the underside of the plateform 8; this prevents the re-extraction of the wick by the withdrawing plunger. A cross-bar 19' rigid with plunger 19 carries guide rods 20 which pass through front and rear wings 18' of portal 18 to steady the position of the plunger; in the vicinity of platform 8 the plunger is additionally guided by vertical rollers 21 engaging its narrow sides.

In FIGS. 4 and 5 I have shown details of the capping station 44. That station comprises a chute 22 for the guidance of a stack of covers 3 sliding toward an entrance end of an arcuately curved tube 23 which lies in a vertical plane perpendicular to rails 33 and is centered on a horizontal shaft 49 serving as a fulcrum for a swingable arm 24. Shaft 49, journaled in a post 50 rigid with the machine frame, is periodically reciprocated by a nonillustrated crank drive synchronized with the various servomotors which control the slider 5, the piston 16 and the plunger 19.

Guide tube 23 has a flattened exit end overhanging the channel between rails 33 just above the path of the upright casings 1 arriving from insertion station 43. Two pneumatic jacks 27 and 28, synchronized with the drive of arm 24, carry rollers 29 and 30 which serve to compress the mouth of each casing against the inserted wick to facilitate the fitting of a cover 3 over that casing. As the casing 1 comes to rest underneath the exit end of tube 23, arm 24 swings counterclockwise to pick up the first cover 3 of the stack descending along chute 22, the covers lying on the chute with their open ends facing upwardly so that these open ends are at the bottom after the cover has traversed an arc of about 150° within tube 23. A pusher 31, forming part of another pneumatic jack 32 properly synchronized with the arm drive, is actuated after the arm 24 has begun its return swing in the clockwise direction; the pusher then drives the cover 3 down around the aligned casing 1, camming aside the rollers 29 and 30 which at this instance are no longer under pressure. The rails 33 are separated more widely at this point then further upstream along the track in order to give passage to the cover.

Another pair of pneumatic servomotors 25, flanking the chute 22, are synchronized with the arm drive to repress the remaining covers 3 of the stack by means of retaining members 26 in order to allow the arm 24 to regain its initial position shown in full lines in FIG. 4. Thereafter, retaining members 26 are again moved outwardly (to the left in FIG. 5) so that the stacked covers 3 may follow suit and align a further cover with the tip of the arm 24 preparatorily to the next feeding stroke.

In FIG. 6 I have shown a turntable 35 served by the four assembly lines 40A – 40D whose principal components 4, 6, 8, 15, 22 and 40 have been supplemented by corresponding suffixes A–D. Turntable 35 rotates counterclockwise and unloads the completed vaporizers, arriving over rails 33A–33D, onto a discharge chute 34 leading to a nonillustrated packaging station. It will be noted that assembly lines 40A and 40D are aligned with each other, as are assembly lines 40C and 40D; the two pairs of aligned assembly lines include with each other an acute angle α, e.g. of 35°, in order to permit the tangential discharge of the finished articles via chute 34 in the direction of divergence of these lines. That discharge path is here shown to be parallel to lines 40C and 40D but could also extend in a different direction. Naturally, the number of assembly lines and their relative orientation may be varied.

I claim:

1. A machine with at least one assembly line for serially producing vaporizers with flat wicks folded into U-shape within open-topped, laterally apertured generally prismatic casings capped by complementary covers which are vertically slidable thereon to control the escape of a volatile liquid impregnating the wicks, said assembly line comprising:
    a frame forming an upper track and a lower track;
    a loading station provided with first feed means for successively depositing dry unfolded wicks on said upper track and advancing said wicks in a row toward a transfer point, said upper track having a discontinuity at said transfer point giving access to said lower track;
    an impregnating station between said loading station and said transfer point provided with distributing means connected to a source of volatile liquid, said distributing means adjoining said upper track for letting a quantity of said liquid permeate each wick arriving from said loading station;
    second feed means for successively depositing empty casings in an upright position on said lower track and advancing said casing past said discontinuity to a downstream location;
    an insertion station at said transfer point provided with plunger means above said upper track synchronized with said first and second feed means and aligned with a transverse centerline of an oncoming wick for forcing the wick through said discontinuity into a casing aligned therewith on said lower track while doubling the wick as it enters the casing; and
    a capping station at said downstream location provided with third feed means synchronized with said first and second feed means for positioning a cover above each oncoming casing, said capping station further including pusher means for thrusting a cover so positioned onto the casing aligned therewith;

2. A machine as defined in claim 1 wherein said first feed means comprises a hopper adapted to hold a stack of unfolded wicks, said magazine resting on said upper track and being provided with aligned slots at the level of the lowest wick of the stack, and a reciprocating slider in line with said slots having a stroke sufficient to dislodge said lowest wick from said magazine.

3. A machine as defined in claim 1 wherein said second feed means comprises conveyor means for delivering the casings to said lower track at a location upstream of said transfer point and piston means at said upstream location for driving each oncoming casing along said lower track in line with other casings previously deposited thereon whereby the entire row of casings is periodically advanced between said upstream and downstream locations.

4. A machine as defined in claim 1 wherein said third feed means comprises an arcuate guide tube with an entrance end laterally offset from said lower track and with an exit end opening onto said lower track, said pusher means traversing said exit end, a chute carrying a stack of covers said entrance end, and a reciprocating arm swingable about the center of curvature of said tube, said arm extending into said tube for successively transporting oncoming covers from said entrance end to said exit end.

5. A machine as defined in claim 4 wherein said chute is provided with retaining means synchronized with said arm for repressing the stack of covers preparatorily to a return of said arm to a starting position adjacent said entrance end.

6. A machine as defined in claim 4, further comprising pressure means beneath said exit end synchronized with said arm for squeezing the top of an aligned casing preparatorily to the fitting of a cover thereon.

7. A machine as defined in claim 1 wherein said impregnating station comprises a top plate overlying said first track with a pair of symmetrical bottom clearances positioned to register with respective halves of a wick passing underneath, said top plate having ports communicating with a source of volatile liquid and with said clearances, and bottom plates in said clearances provided with liquid-distributing perforations.

8. A machine as defined in claim 7 wherein said perforations form a generally rectangular array with additional perforations along a longitudinal centerline of the array.

9. A machine as defined in claim 1 wherein said discontinuity is a slit extending midway along said upper track in the longitudinal direction thereof.

10. A machine as defined in claim 1 with a plurality of substantially identical assembly lines, further comprising a turntable for conveying capped and filled casings to a final destination, said assembly lines having discharge ends opening onto said turntable.

* * * * *